United States Patent
Tadano (10) Patent No.: US 12,279,838 B2
(45) Date of Patent: Apr. 22, 2025

(54) ARM DEVICE, CONTROL METHOD, AND PROGRAM

(71) Applicant: RIVERFIELD INC., Tokyo (JP)

(72) Inventor: Kotaro Tadano, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 1158 days.

(21) Appl. No.: 16/962,658

(22) PCT Filed: Sep. 4, 2019

(86) PCT No.: PCT/JP2019/034771
§ 371 (c)(1),
(2) Date: Jul. 16, 2020

(87) PCT Pub. No.: WO2020/050314
PCT Pub. Date: Mar. 12, 2020

(65) Prior Publication Data
US 2021/0361363 A1 Nov. 25, 2021

(30) Foreign Application Priority Data
Sep. 6, 2018 (JP) .................. 2018-167288

(51) Int. Cl.
*A61B 34/30* (2016.01)
*A61B 17/29* (2006.01)
(Continued)

(52) U.S. Cl.
CPC ............... *A61B 34/30* (2016.02); *A61B 17/29* (2013.01); *A61B 90/50* (2016.02); *B25J 9/02* (2013.01);
(Continued)

(58) Field of Classification Search
CPC ......... A61B 34/30; A61B 17/29; A61B 90/50; A61B 2034/301; A61B 34/71;
(Continued)

(56) References Cited

U.S. PATENT DOCUMENTS

| 10,016,900 B1 | 7/2018 | Meyer et al. |
| 2010/0094312 A1 | 4/2010 | Ruiz Morales et al. |

(Continued)

FOREIGN PATENT DOCUMENTS

| DE | 102010033326 A1 | 2/2012 |
| JP | 2010035768 A | 2/2010 |

(Continued)

OTHER PUBLICATIONS

Extended European Search Report for European Patent Application No. 19858274.4, mailed Sep. 7, 2021, 10 pages.

(Continued)

*Primary Examiner* — Sihar A Karwan
(74) *Attorney, Agent, or Firm* — Withrow + Terranova, PLLC; Vincent K. Gustafson (57) ABSTRACT

An arm device includes a joint portion configured to be rotated to thereby change a position and/or a posture of a surgical tool, and an actuator configured to generate a driving force that rotates the joint portion, and to allow a rotation of the joint portion in accordance with an externally applied force. Moreover, the arm device is configured to estimate an external force applied to the surgical tool, to obtain a value of a driving force of the actuator based on a weight of the surgical tool and the external force, and to control the actuator based on a value of the driving force.

13 Claims, 10 Drawing Sheets

(51) Int. Cl.
*A61B 90/50* (2016.01)
*B25J 9/02* (2006.01)
*B25J 9/10* (2006.01)
*B25J 13/08* (2006.01)

(52) U.S. Cl.
CPC ............ *B25J 9/1065* (2013.01); *B25J 13/085* (2013.01); *A61B 2034/301* (2016.02)

(58) Field of Classification Search
CPC .... A61B 2017/00544; A61B 2090/064; A61B 2090/065; A61B 34/35; A61B 2034/302; B25J 9/02; B25J 9/1065; B25J 13/085; B25J 9/1633; B25J 9/1689; G05B 2219/45118
See application file for complete search history.

(56) References Cited

U.S. PATENT DOCUMENTS

| | | |
|---|---|---|
| 2013/0012930 A1 | 1/2013 | Ruiz Morales et al. |
| 2014/0222204 A1* | 8/2014 | Kawashima ............ A61B 34/76 700/258 |
| 2015/0157409 A1 | 6/2015 | Onuma |
| 2018/0194013 A1* | 7/2018 | Ruiz Morales ........ A61B 34/35 |
| 2019/0105785 A1 | 4/2019 | Meyer et al. |
| 2019/0223967 A1* | 7/2019 | Abbott .................. A61B 34/30 |
| 2020/0039086 A1 | 2/2020 | Meyer et al. |
| 2021/0106396 A1 | 4/2021 | Iceman |

FOREIGN PATENT DOCUMENTS

| | | |
|---|---|---|
| JP | 2015100677 A | 6/2015 |
| JP | 2017104914 A | 6/2017 |
| WO | 2008049898 A1 | 5/2008 |
| WO | 2017083453 A1 | 5/2017 |

OTHER PUBLICATIONS

International Search Report (Form PCT/ISA210) for International Application No. PCT/JP2019/034771, mailed Oct. 21, 2019 (2 pages including English translation).

Written Opinion (Form PCT/ISA/237) for International Application No. PCT/JP2019/034771, mailed Oct. 21, 2019 (4 pages including partial English translation of Box V.

Sackier, J.M., et al., "Robotically assisted laparoscopic surgery," Surgical Endoscopy, vol. 8, pp. 63-66 (1994), Springer-Verlag New York Inc.

Hagn, Ulrich, et al., "DLR MiroSurge: a versatile system for research in endoscopic telesurgery," International Journal for Computer Assisted Radiology and Surgery (Int J CARS), Jun. 13, 2009, 11 pages.

Notification Concerning Transmittal of IPRP (Form PCT/IB/326), International Preliminary Report on Patentability (Form PCT/IB/373), Written Opinion (Form PCT/ISA/237), Notification of Translation of Translation of IPRP (Form PCT/IB/338), and Translation of Written Opinion of the International Searching Authority (Form PCT/ISA/237) for International Application No. PCT/JP2019/034771, mailed Mar. 18, 2021 (11 pages).

\* cited by examiner

ARM DEVICE, CONTROL METHOD, AND PROGRAM

CROSS-REFERENCE TO RELATED APPLICATION

This application is the U.S. national phase under 35 U.S.C. § 371 of International Application No. PCT/JP2019/034771 filed on Sep. 4, 2019, which claims the benefit of Japanese Patent Application No. 2018-167288 filed on Sep. 6, 2018 with the Japan Patent Office, wherein the entire disclosures of the foregoing applications are hereby incorporated by reference herein.

TECHNICAL FIELD

The present disclosure relates to an arm device of a surgery assistant robot used for, for example, endoscopic surgery, a method for controlling an arm device, and a program for controlling an arm device.

BACKGROUND ART

Endoscopic surgery with surgery assistant robots is becoming widely available recently. In endoscopic surgery, a laparoscope, an endoscope, or forceps, for example, (hereinafter also described as a "surgical tool") attached to an arm device of a surgery assistant robot is used.

The arm device has a plurality of joints, and a position and/or a posture of the surgical tool is/are controlled by a rotation of each of the joints. For joints (for example, joints forming a gimbal) of the arm device near the surgical tool, use of joints (in other words, passive joints) that are rotated in accordance with an externally applied force is proposed. In other words, an arm device is proposed in which a position and/or a posture of a surgical tool change(s) in accordance with an externally applied force (see, for example, Non-Patent Document 1).

An arm device is also proposed in which actuators are provided to all joints including joints forming a gimbal, and these joints are formed as joints with high rigidity that are not rotated even when a force is externally applied. In other words, an arm device is also proposed in which a surgical tool can be maintained at a fixed position and in a fixed posture even when a force is externally applied (see, for example, Non-Patent Document 2).

PRIOR ART DOCUMENTS

Non-Patent Documents

Non-Patent Document 1: J. M. Sackier, Y. Wang, "Robotically assisted laparoscopic surgery", Surg Endosc, Springer-Verlag New York Inc., (1994) 8, 63-66

Non-Patent Document 2: Ulrich Hagn et al., "DLR MiroSurge: a versatile system for research in endscopic telesurgery", International Journal of Computer Assisted Radiology and Surgery, Springer, (2010) 5, 183-193

SUMMARY OF THE INVENTION

Problems to be Solved by the Invention

On a subject's body (for example, an abdominal wall) that is a target of endoscopic surgery, a port (or a trocar) into which the surgical tool is inserted is placed. In the case of the arm device disclosed in Non-Patent Document 1, the position and/or the posture of the surgical tool change(s) when a load (in other words, a force) applied to a tip of the surgical tool increases. Since the change is transmitted to the subject's body through the port, a load may be imposed on the subject's body.

The arm device disclosed in Non-Patent Document 2 controls the position and/or the posture of the surgical tool based on the position of the port that the arm device recognizes. If there is an error between the recognized port position and an actual port position, the arm device controls the surgical tool based on an erroneous port position. Consequently, a force is applied to the port, and thereby a load may be imposed on the subject's body.

In one aspect of the present disclosure, it is desirable that a load imposed on the subject's body can be reduced.

Means for Solving the Problems

An arm device according to the present disclosure is configured to support a surgical tool and to control a position and/or a posture of the surgical tool. The arm device comprises a joint portion configured to be rotated to thereby change the position and/or the posture of the surgical tool, an actuator configured to generate a driving force that rotates the joint portion, and to allow a rotation of the joint portion in accordance with an externally applied force, an estimator configured to estimate an external force applied to the surgical tool, a calculator configured to obtain, based on a weight of the surgical tool and the external force estimated by the estimator, a value of the driving force generated in the actuator, and a controller configured to control the driving force of the actuator based on the value of the driving force obtained by the calculator.

A control method according to the present disclosure is intended for controlling an arm device with a rotating joint portion, the arm device being configured to support a surgical tool and to control a position and/or a posture of the surgical tool. The control method comprises estimating an external force applied to the surgical tool, obtaining a value of a driving force generated in an actuator based on a weight of the surgical tool and the external force estimated, and controlling the driving force of the actuator based on a value of the driving force obtained. The actuator is configured to generate the driving force that rotates the joint portion, and to allow a rotation of the joint portion in accordance with an externally applied force.

A program according to the present disclosure is intended for controlling an arm device with a rotating joint portion, the arm device being configured to support a surgical tool and to control a position and/or a posture of the surgical tool. The program enables a computer to achieve a function to estimate an external force applied to the surgical tool, a function to obtain a value of a driving force generated in an actuator based on a weight of the surgical tool and the external force estimated, and a function to control the driving force of the actuator based on the value of the driving force obtained. Moreover, the actuator is configured to generate the driving force that rotates the joint portion, and to allow a rotation of the joint portion in accordance with an externally applied force.

In these configurations, the actuator that allows the rotation of the joint portion in accordance with the externally applied force is used, and the actuator is driven in accordance with the value of the driving force obtained based on the weight of the surgical tool and the external force estimated. Thus, it is possible to reduce a load imposed on a subject's body.

In other words, depending on the weight of the surgical tool and the estimated external force, the arm device supports the surgical tool while maintaining the position and/or the posture of the surgical tool. Moreover, if a force different from the estimated external force is externally applied, the position and/or the posture of the surgical tool supported by the arm device change(s). Thus, it is possible to reduce the load imposed on the subject's body from the surgical tool.

In the aforementioned disclosure, it is desirable that the calculator is configured to obtain, at a position corresponding to a position of a device into which the surgical tool is inserted, the value of the driving force that makes a force acting between the surgical tool and the device equal to or smaller than a specified value.

The aforementioned configuration enables reduction of the load imposed from the surgical tool on the subject's body through the device placed on the subject's body.

In the aforementioned disclosure, it is desirable that the surgical tool comprises a bend portion having a bendable tip, and an actuator for the surgical tool configured to generate a driving force that bends the bend portion, and to allow bending of the bend portion in accordance with an externally applied force, wherein the estimator is configured to estimate the external force applied to the surgical tool based on information on a load in the actuator for the surgical tool.

The aforementioned configuration enables reduction of changes of the position and/or the posture of the surgical tool due to the force applied to the surgical tool.

In the aforementioned disclosure, it is desirable that the surgical tool comprises a bend portion having a bendable tip, and a gas-pressure actuator for the surgical tool configured to generate a driving force that bends the bend portion, and to generate the driving force by a gas externally supplied, wherein the estimator is configured to estimate the external force applied to the tip of the surgical tool based on a pressure of the gas in the gas-pressure actuator for the surgical tool.

The aforementioned configuration enables reduction of changes of the position and/or the posture of the surgical tool due to the force applied to the surgical tool.

In the aforementioned disclosure, it is desirable that the estimator is a sensor disposed in vicinity of a tip of the surgical tool, and configured to estimate the force applied to the surgical tool.

Due to the aforementioned configuration, the value of the driving force of the actuator can be obtained based on the external force acting in vicinity of the tip of the surgical tool. Accordingly, changes of the position and/or the posture of the surgical tool can further reduced.

In the aforementioned disclosure, it is desirable that the actuator is a gas-pressure actuator configured to generate the driving force by a gas externally supplied.

Due to the aforementioned configuration, the rotation of the joint portion can be easily allowed even when a force exceeding the driving force generated by the actuator is applied to the joint portion.

Due to the aforementioned arm device, the control method, and the program, the value of the driving force of the actuator can be obtained based on the weight of the surgical tool and the external force estimated. This can reduce the load imposed on the subject's body.

EXPLANATION OF REFERENCE NUMERALS 10, 110 ... arm device, 21, 121 ... estimator, 22 ... calculator, 23 ... controller, 62 ... first joint portion (joint), 63 ... second joint portion (joint). 64 ... third joint portion (joint), 62a ... first actuator, 63a ... second actuator, 64a ... third actuator, 70 ... surgical tool, 75 ... trocar (device), 76 ... actuator for a surgical tool, 124 ... sensor, $f_t$ ... external force, W ... weight

MODE FOR CARRYING OUT THE INVENTION

Figure 1:
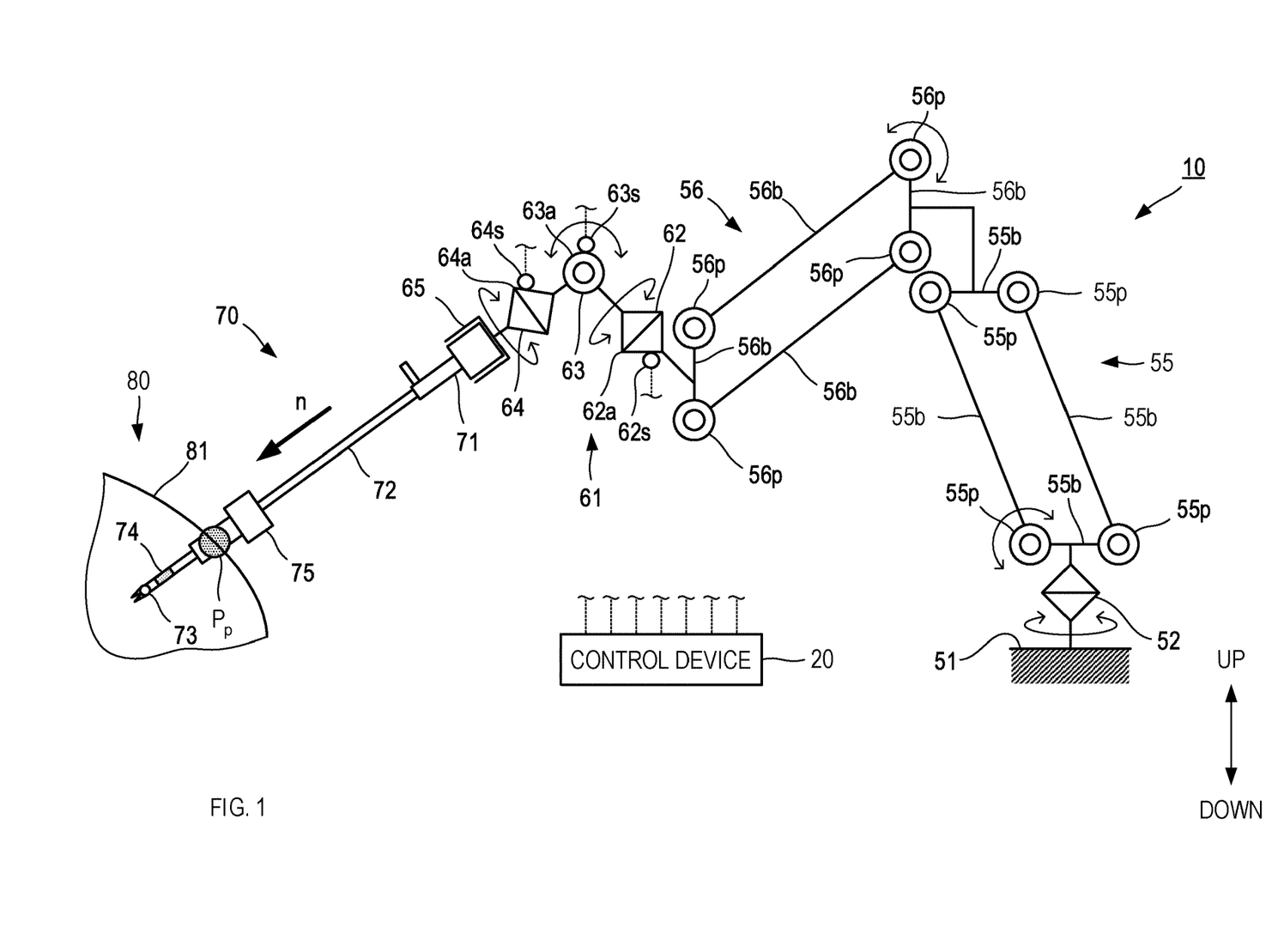
FIG. 1 is a schematic diagram showing a configuration of an arm device according to a first embodiment.

The following describes an arm device 10 according to a first embodiment with reference to FIGS. 1 to 8. As shown in FIG. 1, the arm device 10 is used, for example, a surgery assistant robot for endoscopic surgery in the first embodiment.

The arm device 10 supports a surgical tool 70 such that a position and/or a posture (in other words, orientation) of the surgical tool 70 can be changed. Moreover, the arm device 10 controls the surgical tool 70 such that the surgical tool 70 passes through a pivot position $P_p$ that is a specified relative position to the arm device 10 even when the position and/or the posture of the surgical tool 70 change(s). The pivot position $P_p$ approximately corresponds to a position of a trocar (device) 75 placed at an abdominal wall 81 of a patient (subject's body) 90 undergoing endoscopic surgery. Hereinafter, the trocar 75 will be also described as a port.

The surgical tool 70 may be a tool, such as an endoscope, forceps, and so on used for endoscopic surgery. In the first embodiment, the surgical tool 70 is forceps as one example.

Figure 2:
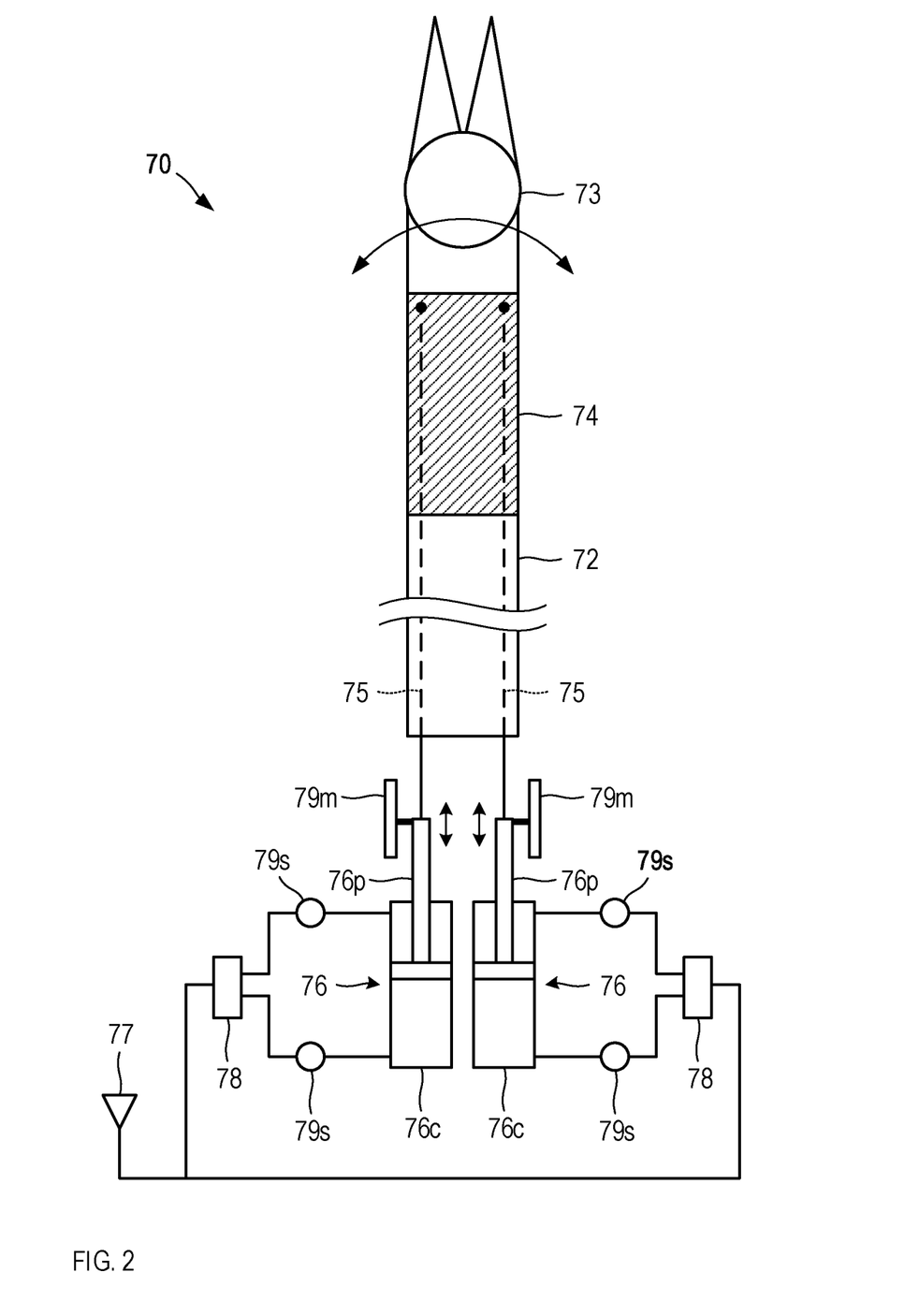
FIG. 2 is a schematic diagram showing a configuration of a surgical tool in FIG. 1.

As shown in FIGS. 1 and 2, the surgical tool 70, which is forceps, mainly comprises a main body 71 and a tubular portion 72. The main body 71 is held by the arm device 10 and accommodates an imaging device that converts images fed through the tubular portion 72 into electronic signals.

The tubular portion 72 extends in a tubular or a rod-like manner so as to be inserted into the trocar 75 and inside the abdominal wall 81 of the patient. Moreover, the tubular portion 72 is configured such that images are transmitted from its leading end to the main body 71.

The tubular portion 72 comprises a leading end portion 73 and a bend portion 74. The leading end portion 73 is inserted into the body of the patient 80. In the first embodiment, the leading end portion 73 comprises a part configured to pinch a target as one example.

The bend portion 74 is formed into a tubular or a columnar shape, and is provided with the leading end portion 73 at a first end and the tubular portion 72 at a second end. The bend portion 74 is configured to bend in a transverse direction with respect to a direction in which the tubular portion 72 extends. A known configuration, but not particularly limited thereto, may be used for the bend portion 74.

Furthermore, the surgical tool 70 mainly comprises wires 74a used for bending the bend portion 74, and actuators 76 for the surgical tool. In the first embodiment, two sets of a combination of the wire 74a, the actuator 76 for the surgical tool, and a valve 78 are provided as one example. Nevertheless, one, three, or more sets of the aforementioned combination may be provided.

The wires 74a are each formed in a rope-like manner, and each has a first end connected to the bend portion 74, and a second end connected to the actuator 76 for the surgical tool so as to transmit a driving force generated by the actuator 76 for the surgical tool to the bend portion 74.

The actuators 76 for the surgical tool generate driving forces that bend the bend portion 74. The actuators 76 for the surgical tool are configured as, for example, gas-pressure actuators that generate the driving forces by an externally supplied gas (for example, air). Moreover, the actuators 76 for the surgical tool are configured to allow bending of the bend portion 74 in accordance with an externally applied force. Each of the actuators 76 for the surgical tool mainly comprise a piston 76p and a cylinder 76c.

The piston 76p is disposed to be linearly movable relative to the cylinder 76c. To a portion of the piston 76p projecting from the cylinder 76c, the second end of the wire 74a is connected. A potentiometer 79m that measures displacement of the piston 76p is disposed facing the piston 76p.

The cylinder 76c is a tubular member having both ends closed. The internal space of the cylinder 76c is divided into two sections by the piston 76p. The cylinder 76c is provided with piping that supplies pressurized air provided from an air supplier 77 to each of the sections.

Between the cylinder 76c and the air supplier 77, the valve 78 that controls a receiver of the pressurized air from the air supplier 77 and two pressure sensors 79s each of which measures an air pressure in each section of the cylinder 76c are provided.

The valve 78 selects one of the two sections of the cylinder 76c to supply the pressurized air. The valve 78 may have a known configuration.

The pressure sensors 79s are disposed between the valve 78 and the cylinder 76c so as to respectively measure the air pressures in the corresponding sections. The measured air pressures are outputted to the control device 20.

As shown in FIG. 1, the arm device 10 mainly comprises a rotating portion 52, a first link portion 55, a second link portion 56, a gimbal portion 61, a holding portion 65, and the control device 20. The rotating portion 52, the first link portion 55, and the second link portion 56 are driven based on control signals inputted from, for example, a controller (not shown) of the arm device 10.

The rotating portion 52 is a joint disposed at a position where the arm device 10 is secured to a base 51. The rotating portion 52 is configured to be rotationally driven about a rotational axis extending in an up-down direction, and the specific configuration thereof is not limited.

The first link portion 55 is disposed between the rotating portion 52 and the second link portion 56, and is driven by an actuator (not shown). The first link portion 55 comprises two pairs of parallel bars 55b. The bars 55b are arranged in a rectangular manner, and two adjacent bars 55b are joined by pins 55p that allow a rotation of a single degree of freedom system. In the first embodiment, the first link portion 55 is disposed to extend in the up-down direction as one example.

The second link portion 56 is disposed between the first link portion 55 and the gimbal portion 61, and is driven by an actuator (not shown). Similarly to the first link portion 55, the second link portion 56 comprises two pairs of parallel bars 56b. The bars 56b are arranged in a rectangular manner, and two adjacent bars 56b are joined by pins 56p that allow a rotation of a single degree of freedom system. In the first embodiment, the second link portion 56 is disposed to extend in a transverse direction (a direction along a plane intersecting with the up-down direction) as one example.

As shown in FIG. 1, the gimbal portion 61 is disposed between the second link portion 56 and the holding portion 65, and comprises at least one joint portion and at least one actuator. The actuator is provided to each of the at least one joint portion. For example, the gimbal portion 61 comprises a first to a third joint portions (joints) 62 to 64, respectively having rotational axes intersecting with each other, and a first to a third actuators 62a to 64a. The number of the joint portions and that of the actuators provided in the gimbal portion 61 are not limited to three, but can be suitably determined.

As shown in FIG. 1, the first joint portion 62 is disposed adjacent to the second link portion 56. The first joint portion 62 is disposed such that the rotational axis thereof extends obliquely upward. More preferably, the first joint portion 62 is disposed such that the rotational axis thereof extends obliquely upward at an angle of 45° with respect to a horizontal plane.

The second joint portion 63 is disposed between the first joint portion 62 and the third joint portion 64. The third joint portion 64 is disposed adjacent to the holding portion 65. The first to the third joint portions 62 to 64 are only required to be respectively rotatable about the rotational axes thereof, and the configurations of the first to the third joint portions 62 to 64 are not particularly limited.

As shown in FIG. 1, the first actuator 62a is disposed close to the first joint portion 62 so as to rotationally drive the first joint portion 62 and to control a rotation angle of the first joint portion 62. Moreover, the first actuator 62a is configured as a gas-pressure actuator that generates a driving force by an externally supplied gas (for example, air).

The first actuator 62a is a rotary air-pressure actuator and directly generates torque that rotationally drives the first joint portion 62. The first actuator 62a has, but not particularly limited to, a known configuration.

The first actuator 62a comprises a first pressure sensor 62s. The first pressure sensor 62s measures an air pressure in the first actuator 62a. The value of the measured air pressure is outputted to an estimator 21 of the control device 20. The first pressure sensor 62s has, but not particularly limited to, a known configuration.

The second actuator 63a is disposed close to the second joint portion 63 so as to rotationally drive the second joint portion 63 and to control a rotation angle of the second joint portion 63. Moreover, the second actuator 63a is configured as a gas-pressure actuator that generates a driving force by an externally supplied gas (for example, air).

The second actuator 63a is a rotary air-pressure actuator and directly generates torque that rotationally drives the second joint portion 63. The second actuator 63a has, but not particularly limited to, a known configuration.

The second actuator 63a comprises a second pressure sensor 63s. The second pressure sensor 63s measures an air pressure in the second actuator 63a. The value of the measured air pressure is outputted to the estimator 21 of the control device 20. The second pressure sensor 63s has, but not particularly limited to, a known configuration.

The third actuator 64a is disposed close to the third joint portion 64 so as to rotationally drive the third joint portion 64 and to control the rotation angle of the third joint portion 64. Moreover, the third actuator 64a is configured as a gas-pressure actuator that generates a driving force by an externally supplied gas (for example, air).

The third actuator 64a is a rotary air-pressure actuator and directly generates torque that rotationally drives the third joint portion 64. The third actuator 64a has, but not particularly limited to, a known configuration.

The third actuator 64a comprises a third pressure sensor 64s. The third pressure sensor 64s measures an air pressure in the third actuator 64a. The value of the measured air pressure is outputted to the estimator 21 of the control device 20. The third pressure sensor 64s has, but not particularly limited to, a known configuration.

The holding portion 65 is disposed at a position adjacent to the gimbal portion 61, in other words, disposed at the leading end of the arm device 10. The holding portion 65 is configured to hold the surgical tool 70, but the specific configuration of the holding portion 65 is not particularly limited.

Figure 3:
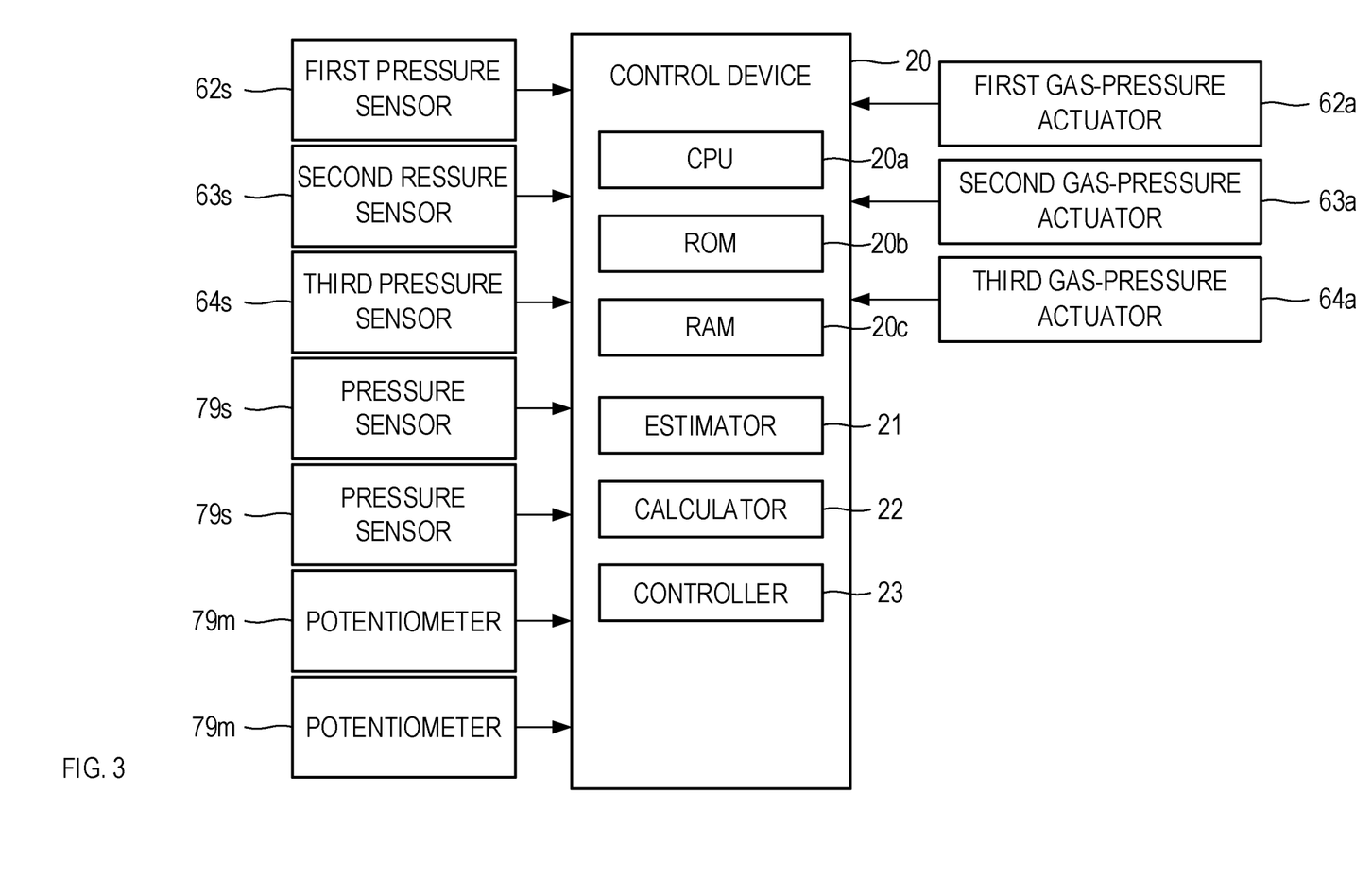
FIG. 3 is a block diagram of a control device in FIG. 1.

The control device 20 controls the arm device 10. As shown in FIGS. 1 and 3, the control device 20 is configured as an information processing device, such as a computer, comprising a CPU (Central Processing Unit) 20a, a ROM 20b, a RAM 20c, and an input-output interface. The CPU 20a executes programs stored in the ROM 20b, or programs loaded to the RAM 20c. Functions of at least the estimator 21, a calculator 22, and a controller 23 can be carried out through execution of the programs. In this embodiment, the ROM 20b or the RAM 20c corresponds to a non-transitory tangible storage medium storing the programs. The control device 20 may comprise an electronic circuit (for example, an integrated circuit such as an ASIC) without a CPU so as to entirely or partially achieve the function of the control device 20 by the electronic circuit.

The estimator 21 estimates an external force $f_t$ applied to the surgical tool 70. In the first embodiment, the estimator 21 performs an arithmetic process based on, for example, the air pressures in the actuators 76 for the surgical tool to estimate the external force $f_t$ applied to the surgical tool 70. The specific way of estimating the external force $f_t$ will be described later.

The calculator 22 performs an arithmetic process to obtain values of the driving forces respectively generated in the first to the third actuators 62a to 64a based on a weight W of the surgical tool 70 and the external force $f_t$ estimated by the estimator 21. Specific details of the arithmetic process will be described later.

To obtain the values of the driving forces, the calculator 22 may use a mass of the surgical tool 70 in place of the weight W of the surgical tool 70. In this case, the calculator 22 may calculate the weight W using the mass of the surgical tool 70 and gravitational acceleration, and obtain the values of the driving forces using the calculated weight W.

The controller 23 controls the driving forces respectively generated in the first to the third actuators 62a to 64a based on the values of the driving forces obtained by the calculator 22. Specific details of control by the controller 23 will be described later.

The following describes the details of control performed in the arm device 10 configured as described above with reference to FIGS. 4 to 7.

Figure 4:
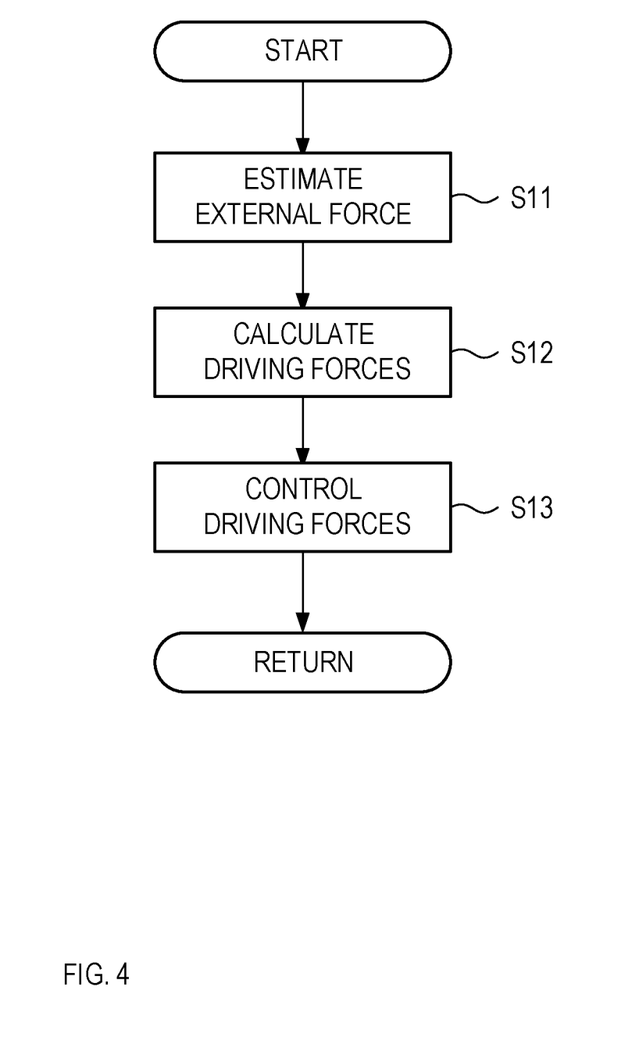
FIG. 4 is a flowchart of a process performed by the control device in FIG. 1.

As shown in FIG. 4, the estimator 21 of the control device 20 first performs an arithmetic process to estimate the external force $f_t$ (S11). In the first embodiment, the external force $f_t$ is, for example, a force acting on the tip of the surgical tool 70 inserted into the patient 80. In other words, the external force $f_t$ is, for example, a force that acts in reaction to interference between the surgical tool 70 and the patient 80. In a case, for example, where the surgical tool 70 comprises a movable portion such as forceps, the external force $f_t$ is a force that acts in reaction to movement of the surgical tool 70.

Specifically, the estimator 21 acquires, for example, air pressure information (values) outputted from the pressure sensors 79s provided to the actuators 76 for the surgical tool, and/or displacement information of the pistons 76p from the potentiometers 79m. Subsequently, the estimator 21 performs the arithmetic process to estimate the external force $f_t$ based on the acquired air pressure information and/or the displacement information of the pistons 76p. The arithmetic process may be, but not particularly limited to, a known method.

Upon estimation of the external force $f_t$, the calculator 22 of the control device 20 performs an arithmetic process to obtain the values of the driving forces respectively generated in the first to the third actuators 62a to 64a of the gimbal portion 61 (S12).

Figure 5:
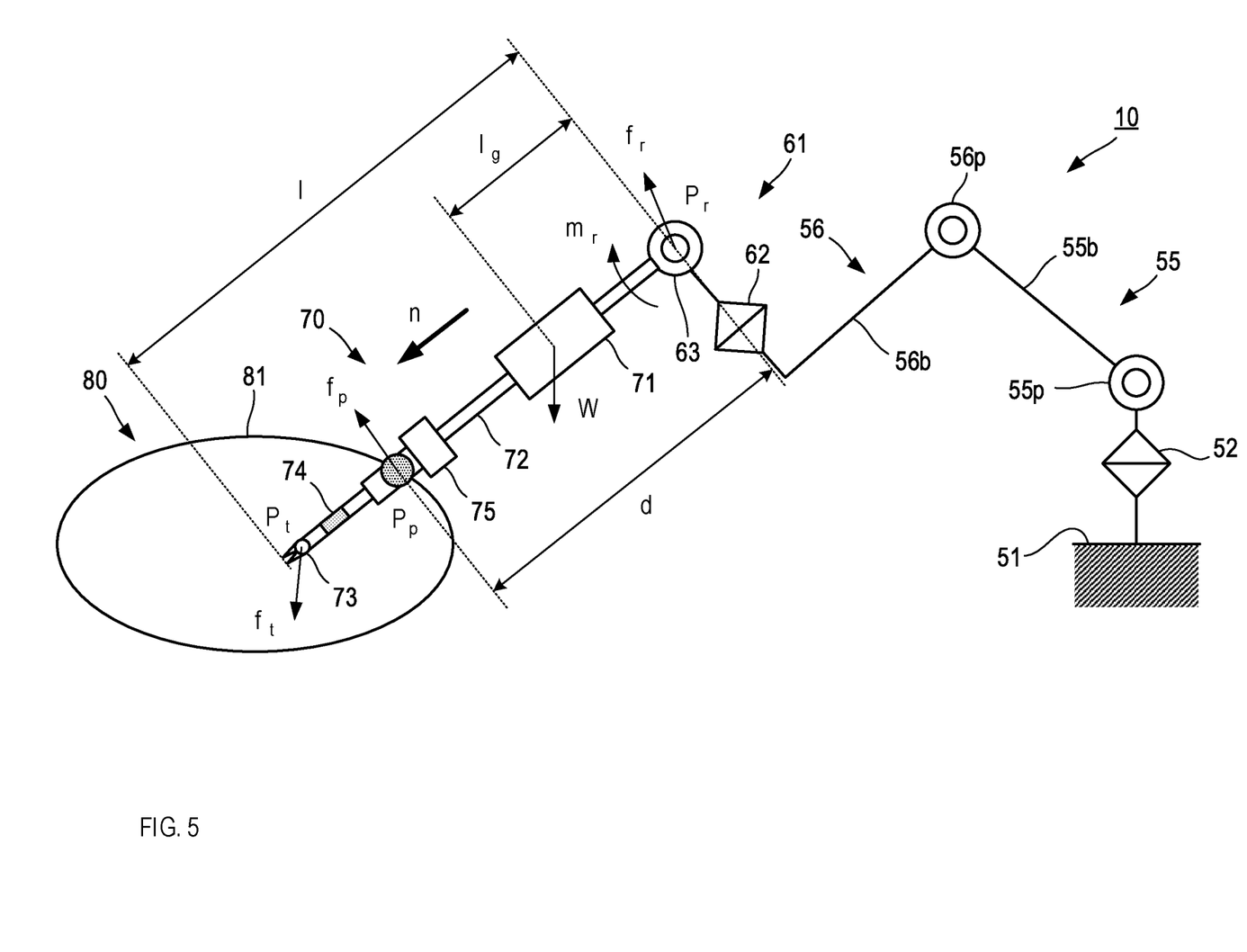
FIG. 5 is a schematic diagram showing parameters of the arm device in FIG. 1.

The following describes the arithmetic process to obtain the values of the driving forces with reference to FIG. 5. The values of the driving forces are calculated based on a moment $m_r$ produced in the gimbal portion 61 which will be described below. In FIG. 5, the configuration of the arm device 10 is simplified to facilitate understanding.

First, each parameter will be explained. l represents a length (entire length) from a rear end $P_r$ to a tip $P_t$ of the surgical tool 70. d represents a length from the rear end $P_r$ to the pivot position $P_p$ of the surgical tool 70. $l_g$ represents a length from the rear end $P_r$ to a center of gravity of the surgical tool 70. These values may be stored in advance in the control device 20, or may be obtained in accordance with a known calculation method.

In the first embodiment, a point of reference when the surgical tool 70 is controlled is the rear end $P_r$ of the surgical tool 70 as one example. However, the point of reference may be the tip $P_t$ of the surgical tool 70, or other positions.

An insertion direction n of the surgical tool 70 corresponds to a longitudinal direction (in other words, axis direction) of the surgical tool 70. The insertion direction n is expressed by Formula (1), which will be explained later, with a vector indicating a position of the pivot position $P_p$ and a vector indicating a position of the rear end $P_r$ of the surgical tool 70.

Specifically, the insertion direction n is obtained by dividing a direction vector, which is obtained by subtracting the vector indicating the position of the rear end $P_r$ from the vector indicating the position of the pivot position $P_p$, by the absolute value of the direction vector.

Moreover, the tip $P_t$ of the surgical tool 70 is expressed by Formula (2) below with the entire length l of the surgical tool 70, the insertion direction n, and the rear end $P_r$ of the surgical tool 70. Specifically, a vector indicating the position of the tip $P_t$ is obtained by adding the vector indicating the position of the rear end $P_r$ to a vector, which is obtained by multiplying the entire length l by the insertion direction n.

To express the pivot position $P_p$, and the position of the rear end $P_r$ of the surgical tool 70, a value calculated based on, for example, rotation angles of the rotating portion 52 of the arm device 10, the first link portion 55, the second link portion 56, and so on may be used, or other measured values may be used.

[Mathematical Formula 1]

$$n = \frac{P_p - P_r}{|P_p - P_r|} \quad (1)$$

[Mathematical Formula 2]

$$P_i = \ln + P_r \quad (2)$$

Furthermore, a balance of forces on the surgical tool 70 is expressed by Formula (3) below, and a balance of moments is expressed by Formula (4) below where $f_t$ represents the external force that is a force acting on the tip $P_t$ of the surgical tool 70, and $f_p$ represents a force acting on the pivot position $P_p$ of the surgical tool 70. In addition, $f_r$ represents a force acting on the rear end $P_r$ of the surgical tool 70, and W represents a force acting on the center of gravity of the surgical tool 70. $m_r$ represents a moment produced in the gimbal portion 61.

[Mathematical Formula 3]

$$f_t + f_p + f_r + W = 0 \quad (3)$$

[Mathematical Formula 4]

$$\ln \times f_t + l_p n \times f_p + l_g n \times W + m_r = 0 \quad (4)$$

Formula (3) indicates that a total of the force $f_t$ acting on the tip $P_t$, the force $f_p$ acting on the pivot position $P_p$, the force $f_r$ acting on the rear end $P_r$, and the force W acting on the center of gravity of the surgical tool 70 is zero. In other words, Formula (3) indicates that the forces acting on the surgical tool 70 are balanced.

Formula (4) indicates that a total of a moment $\ln \times f_t$ resulting from the force $f_t$ acting on the tip $P_t$, a moment $l_p n \times f_p$ resulting from the force $f_p$ acting on the pivot position $P_p$, a moment $l_g n \times W$ resulting from the force W acting on the center of gravity of the surgical tool 70, and the moment $m_r$ produced in the gimbal portion 61 is zero. In other words, Formula (4) indicates that the moments acting on the surgical tool 70 are balanced.

The calculator 22 of the control device 20 performs the arithmetic process to obtain the values of the driving forces when the force $f_p$ at the pivot position $P_p$ becomes zero. Specifically, the calculator 22 calculates the moment $m_r$ produced in the gimbal portion 61 based on Formula (5) below, in which zero is substituted for $f_p$ in the aforementioned Formula (4) and the equation is arranged.

[Mathematical Formula 5]

$$m_r = -\ln \times f_t - l_g n \times W \quad (5)$$

In the above-described arithmetic process, the moment $m_r$ is obtained, under an ideal condition where the force $f_p$ at the pivot position $P_p$ becomes zero, as one example. Nevertheless, an arithmetic process may be performed to obtain the moment $m_r$ produced when the force $f_p$ is not zero, but equal to or less than a specified value. For example, the specified value may be determined based on a load that is allowable on, for example, the abdominal wall 81 of the patient 80.

Having obtained the values of the driving forces, the controller 23 of the control device 20 performs the arithmetic process to control the driving forces respectively generated in the first to the third actuators 62a to 64a of the gimbal portion 61 based on the obtained values of the driving forces (S13).

Specifically, a process to control the air pressures respectively in the first to the third actuators 62a to 64a is performed. A known method, but not particularly limited thereto, can be used for a method for controlling the air pressures.

In the arm device 10 configured as described above, the first to the third actuators 62a to 64a that respectively allow rotations of the first to the third joint portions 62 to 64 in accordance with externally applied forces are used. Moreover, the first to the third actuators 62a to 64a are driven in accordance with the values of the driving forces obtained based on the weight W of the surgical tool 70 and the estimated external force $f_t$. Thus, it is possible to reduce the load imposed on the patient 80.

In other words, depending on the weight W of the surgical tool 70 and the estimated external force $f_t$, the arm device 10 supports the surgical tool 70 while maintaining the position and/or the posture of the surgical tool 70. On the other hand, when a force different from the estimated external force $f_t$ is externally applied, the position and/or the posture of the surgical tool 70 supported by the arm device 10 change(s). Accordingly, it is possible to reduce the load imposed on the patient 80 from the surgical tool 70.

Figure 6:
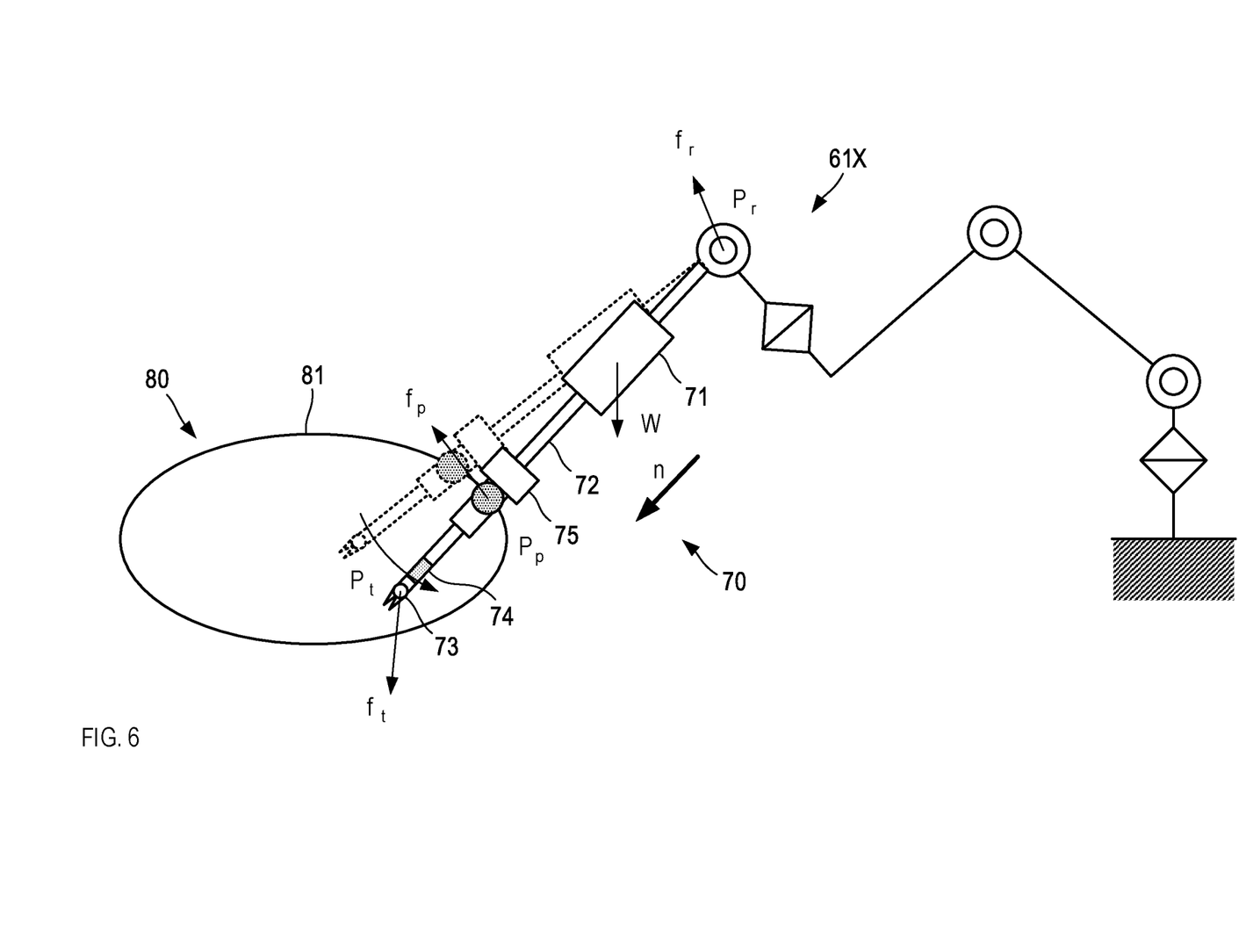
FIG. 6 is a schematic diagram showing a behavior of the surgical tool, in a case where a gimbal portion comprises passive joints.

For example, assume that each of the joint portions of a gimbal portion 61X is configured as a passive joint. That is, assume that the gimbal portion 61X does not comprise the first to the third actuators 62a to 64a and each of the joint portions is freely rotated in response to an external force. In this case, when a force different from the estimated external force $f_t$ is externally applied to the surgical tool 70, the position and/or the posture of the surgical tool 70 change(s), for example, as shown in FIG. 6. FIG. 6 shows that the surgical tool 70 shown with dotted lines is displaced by the different force to the position of the surgical tool 70 shown with solid lines In this case, the load imposed on the abdominal wall 81 from the surgical tool 70 through the trocar 75 increases, and the load imposed on the patient 80 increases.

The arm device 10 according to the first embodiment can inhibit an increase of such a load. If the actual external force $f_t$ is larger than the estimated external force $f_t$, it can be the case where a force different from the estimated external force $f_t$ is applied to the surgical tool 70.

Figure 7:
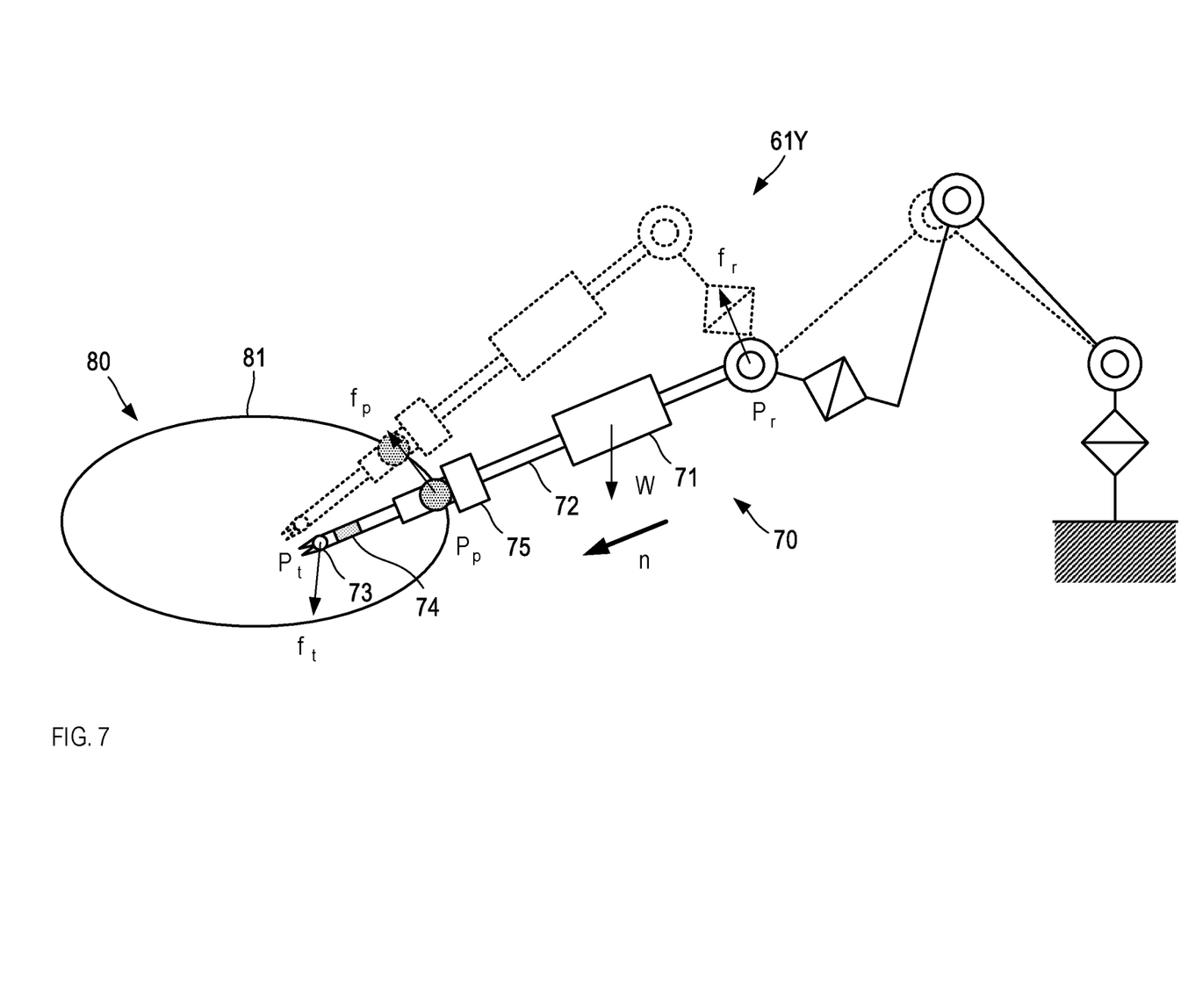
FIG. 7 is a schematic diagram showing a behavior of the surgical tool, in a case where the gimbal portion comprises joints with high rigidity.

Moreover, for example, assume that each of the joint portions of a gimbal portion 61Y is configured as a joint with high rigidity. That is, assume that each of the joint portions of the gimbal portion 61Y comprises an actuator that is different from the gas-pressure actuator, and is not rotated in response to a force being externally applied. Assume, in this case, that a difference is caused, as shown in FIG. 7, between the position and/or posture (shown with the solid lines) of the surgical tool 70 estimated by the arm device 10 and the actual position and/or the actual angle (shown with dotted lines). In such a case, the load imposed on the abdominal wall 81 from the surgical tool 70 through the trocar 75 increases, and the load imposed on the patient 80 increases.

Moreover, the values of the driving forces when the force acting on the surgical tool 70 becomes equal to or smaller than the specified value are obtained in the first embodiment. Accordingly, it is possible to reduce the load imposed on the patient 80 from the surgical tool 70 through the trocar 75 placed on the patient 80.

Furthermore, the external force $f_t$ applied to the surgical tool 70 is estimated based on the air pressures in the actuators 76 for the surgical tool in the first embodiment. Accordingly, it is possible to reduce changes of the position and/or the posture of the surgical tool 70 due to the force applied to the surgical tool 70 (the external forces measured by the pressure sensors 79s).

Additionally, in the first embodiment, the external force $f_t$ applied to the surgical tool 70 is estimated based on the air pressures measured by the pressure sensors 79s as one example. However, the air pressures (in other words, information on the load) supplied to the actuators 76 for the surgical tool may be acquired without using the pressure sensors 79s. The external force $f_t$ applied to the surgical tool 70 may be estimated based on such air pressures.

Moreover, the gas-pressure actuators are used as the first to the third actuators 62a to 64a in the first embodiment. Accordingly, rotations of the first to the third joint portions 62 to 64 to which forces exceeding the driving forces generated by these actuators are applied are easily allowed.

In the first embodiment, the gimbal portion 61 comprises the first to the third actuators 62a to 64a as one example. However, the actuators provided to the gimbal portion 61 are only required to be configured to allow rotations of the first to the third joint portions 62 to 64 in accordance with externally applied forces, and the configurations of the actuators are not particularly limited.

In the first embodiment, the first to the third actuators 62a to 64a are configured as rotary air-pressure actuators as one example. However, these actuators may have configurations shown in FIG. 8.

Figure 8:
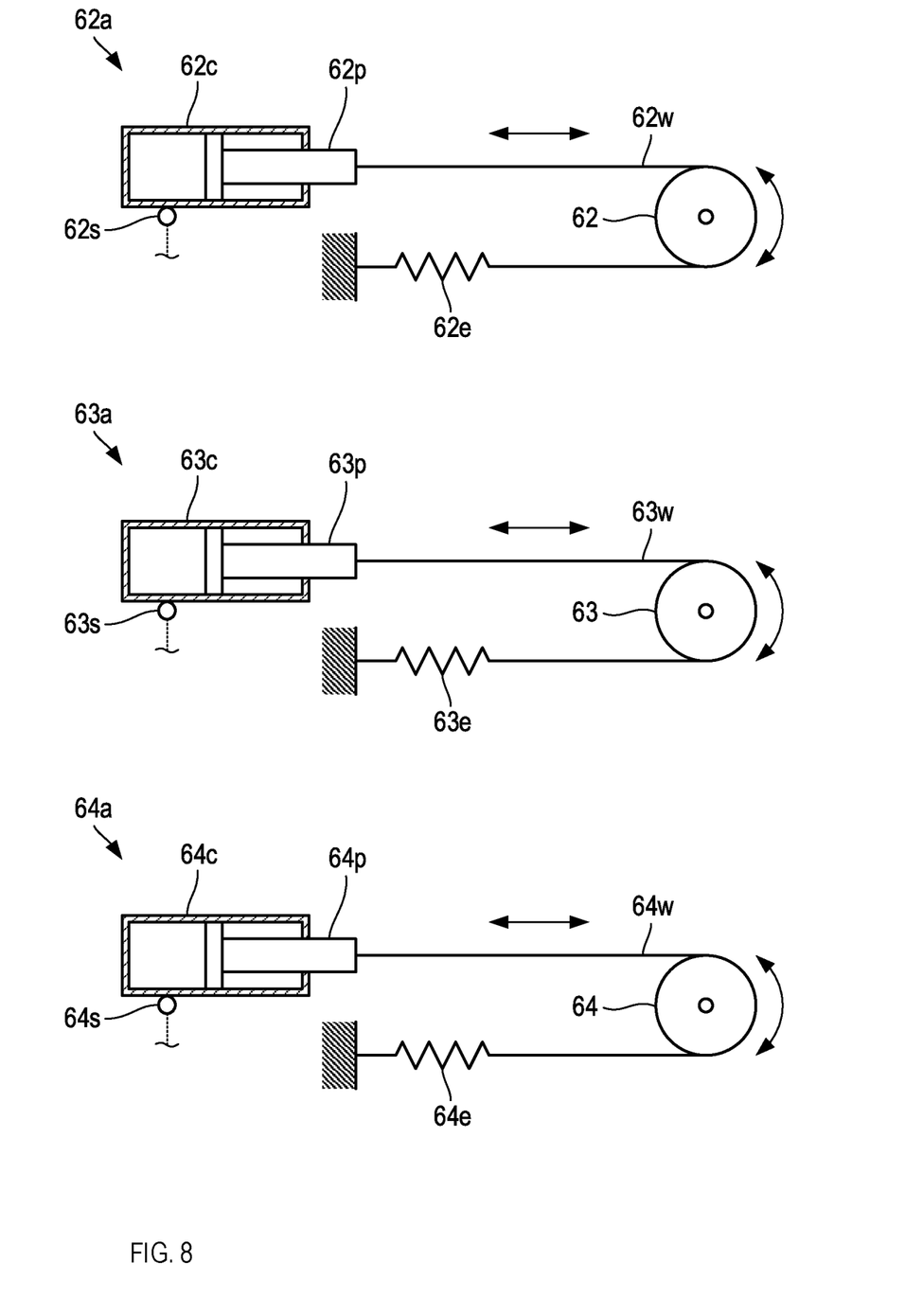
FIG. 8 are schematic diagrams showing configurations of gas-pressure actuators disposed in the gimbal portion in FIG. 1.

In other words, the first actuator 62a may mainly comprise a first cylinder 62c, a first piston 62p, a first wire 62w, a first elastic body 62c, and a first pressure sensor 62s.

The first cylinder 62c is a tubular member having both ends closed. The internal space of the first cylinder 62c is divided into two sections by the first piston 62p. At least one of the sections is configured such that pressurized air can be introduced from outside.

The first piston 62p is disposed to be linearly movable relative to the first cylinder 62c. Moreover, to a portion of the first piston 62p projecting from the first cylinder 62c, the first end of the first wire 62w is connected.

The first wire 62w is formed in a rope-like manner, and transmits movement of the first piston 62p to the first joint portion 62. The first end of the first wire 62w is connected to the first piston 62p, and the second end is connected to the first elastic body 62e. The central area of the first wire 62w is wound around the first joint portion 62.

The first elastic body 62e is a member with elasticity such as a spring, and supports the first wire 62w such that the first wire 62w can be moved in accordance with the movement of the first piston 62p. The first elastic body 62e may be, but not particularly limited to, a known member.

The second actuator 63a may mainly comprise a second cylinder 63c configured similarly to the first actuator 62a, a second piston 63p, a second wire 63w, a second elastic body 63e, and a second pressure sensor 63s. The detailed description of these members is omitted.

The third actuator 64a may mainly comprise a third cylinder 64c configured similarly to the first actuator 62a, a third piston 64p, a third wire 64w, a third elastic body 64c, and the third pressure sensor 64. The detailed description of these members is omitted.

Second Embodiment

Figure 9:
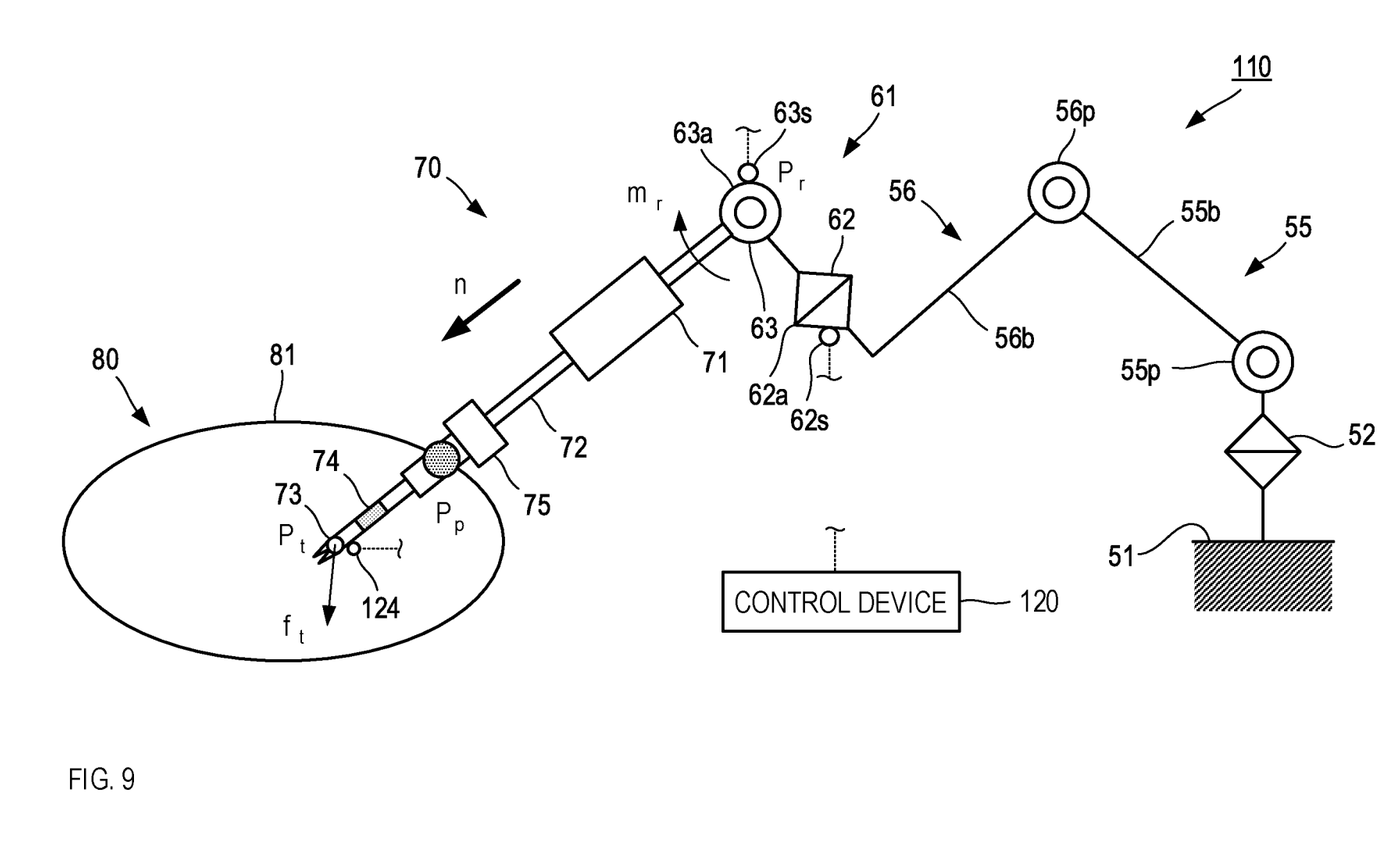
FIG. 9 is a schematic diagram showing a configuration of an arm device according to a second embodiment.
Figure 10:
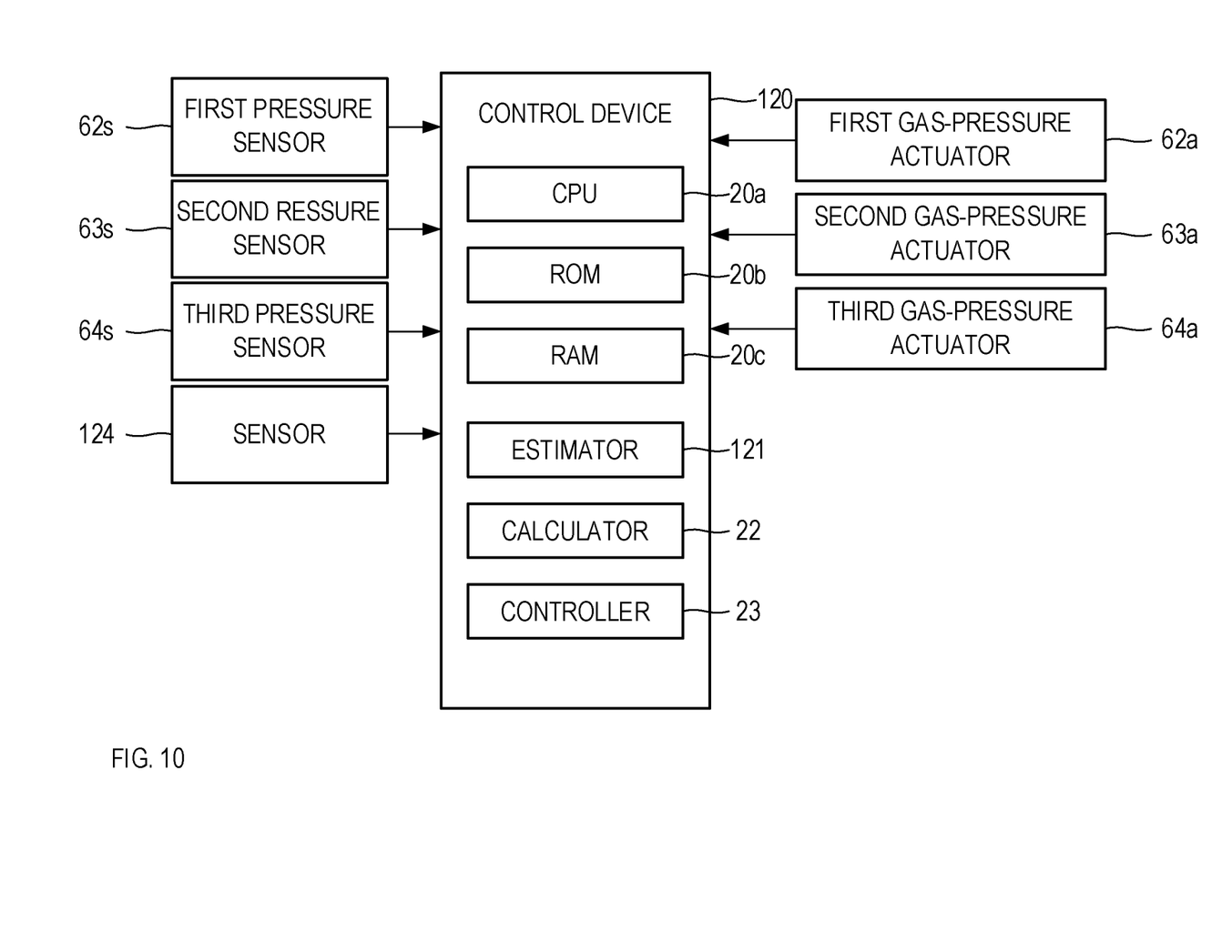
FIG. 10 is a block diagram of a control device in FIG. 9.

The following describes an arm device according to a second embodiment with reference to FIGS. 9 and 10. The basic configuration of the arm device according to the second embodiment is the same as that in the first embodiment, but the position of a sensor used to estimate the external force $f_t$ applied to the surgical tool is different from that in the first embodiment. Thus, the configuration related to the senor will be described using FIGS. 9 and 10, and description of other parts will be omitted in the second embodiment.

As shown in FIGS. 9 and 10, a control device 120 of an arm device 110 according to the second embodiment estimates the external force $f_t$ applied to the surgical tool 70 based on a result of detection by the a sensor 124 disposed in vicinity of the tip $P_t$ of the surgical tool 70. The sensor 124 has a known configuration to detect a force acting in vicinity of the tip $P_t$ of the surgical tool 70, and a way of detection is not particularly limited. The information of the force acting in vicinity of the tip $P_t$ of the surgical tool 70 detected by the sensor 124 is outputted to an estimator 121 of the control device 120.

The estimator 121 performs an arithmetic process to estimate the external force $f_t$ applied to the surgical tool 70 based on the force acting in vicinity of the tip $P_t$ of the surgical tool 70. The estimator 121 performs an arithmetic process and the like to, for example, correct a difference between the position of the sensor 124 and the position on which the external force $f_t$ is acting.

The details of control performed in the arm device 110 according to the second embodiment is the same as that in the first embodiment except that the arithmetic process by the estimator 121 to estimate the external force $f_t$ applied to the surgical tool 70 is different. Description of the same part is omitted.

With the arm device 110 according to the second embodiment, the values of the driving forces are obtained based on the force acting in vicinity of the tip $P_t$ of the surgical tool 70, since the sensor 124 is disposed in vicinity of the tip $P_t$ of the surgical tool 70. Accordingly, it is possible to reduce changes of the position and/or the posture of the surgical tool 70 due to the force applied in vicinity of the tip $P_t$ of the surgical tool 70 (the external force measured by the sensor 124).

The technical scope of the present disclosure is not limited to the aforementioned embodiments, and various modifications can be made to an extent without departing from the gist of the present disclosure. For example, the control device 20 may be integrally configured with the arm device 10, or may be configured separately from the arm device 10 in the aforementioned embodiments.

In addition to the above-described control device 20, the present disclosure can be carried out in various forms including a system having the control device 20 as its component, a program for a computer to function as the control device 20, a non-transitory tangible storage medium, such as a semiconductor memory, that stores the program, and a method that corresponds to the processes performed by the control device 20.

The invention claimed is:

1. An arm device supporting a surgical tool and configured to control a position and/or a posture of the surgical tool, the arm device comprising:
   a joint portion configured to be rotated to thereby change the position and/or the posture of the surgical tool;
   a rotary actuator configured to generate an actuator driving force that exerts a torque that rotates the joint portion;
   an estimator configured to estimate an external force applied to the surgical tool;

a calculator configured to obtain, based on a weight of the surgical tool and the external force estimated by the estimator, a value of the actuator driving force; and a controller configured to control the actuator driving force, and thereby rotate the joint portion, based on the value of the actuator driving force obtained by the calculator;

wherein the surgical tool comprises a bend portion, the bend portion being configured to bend in a transverse direction away from a longitudinal direction of the surgical tool, and the surgical tool comprises a surgical tool actuator configured to generate a bend portion driving force that bends the bend portion;

wherein the estimator is configured to estimate the external force applied to the surgical tool using information on a load supplied to the surgical tool actuator; and wherein forces acting on the arm device satisfy the following formulas:

$$f_t + f_p + f_r + W = 0$$

$$l n \times f_t + l_p n \times f_p + l_g n \times W + m_r = 0$$

according to which:

$$m_r = -l n \times f_t - l_g n \times W,$$

$f_t$ represents a force acting on a tip of the surgical tool,
$f_p$ represents a force acting on a pivot position of the surgical tool,
$f_r$ represents a force acting on a rear end of the surgical tool,
W represents a force acting on a center of gravity of the surgical tool,
$m_r$ represents a moment produced in the joint portion,
$ln \times f_t$ represents a moment resulting from $f_t$,
$l_p n \times f_p$ is a moment resulting from $f_p$, and
$l_g n \times W$ is a moment resulting from W.

2. The arm device according to claim 1, wherein the calculator is configured to obtain the value of the actuator driving force that makes a force, acting on the surgical tool at a position corresponding to a position of a device into which the surgical tool is inserted, equal to or smaller than a specified value.

3. The arm device according to claim 1, wherein:
the surgical tool actuator comprises a gas-pressure actuator configured to generate the bend portion driving force with an externally supplied gas, and wherein the information on the load supplied to the surgical tool actuator is based on a pressure of gas in the gas-pressure actuator.

4. The arm device according to claim 1, wherein the estimator is disposed in vicinity of a tip of the surgical tool and is configured to estimate the external force using signals obtained from a sensor configured to measure a force applied to the surgical tool.

5. The arm device according to claim 1, wherein the surgical tool actuator comprises a gas-pressure actuator configured to generate the bend portion driving force with an externally supplied gas.

6. The arm device according to claim 1, wherein the surgical tool comprises a leading end portion configured to pinch a target tissue, and the bend portion is arranged between the leading end portion and the joint portion.

7. The arm device according to claim 1,
wherein the rotary actuator includes a gas-pressure actuator configured to directly generate the actuator driving force.

8. A method for controlling an arm device with a rotating joint portion and supporting a surgical tool, the arm device being configured to control a position and/or a posture of the surgical tool, the method comprising the steps of:

estimating an external force applied to the surgical tool;
obtaining a value of an actuator driving force generated by an actuator based on a weight of the surgical tool and the estimated external force applied to the surgical tool; and
controlling the actuator driving force of based on the obtained value of the actuator driving force;
wherein the actuator comprises a rotary actuator configured to generate the actuator driving force that exerts a torque that rotates the joint portion, and configured to allow a rotation of the joint portion in accordance with an externally applied force;
wherein the surgical tool comprises a bend portion, the bend portion being configured to bend in a transverse direction away from a longitudinal direction of the surgical tool, the surgical tool comprises a surgical tool actuator configured to generate a bend portion driving force that bends the bend portion, and the method further comprises estimating the external force applied to the surgical tool using information on a load supplied to the surgical tool actuator; and
wherein forces acting on the arm device satisfy the following formulas:

$$f_t + f_p + f_r + W = 0$$

$$l n \times f_t + l_p n \times f_p + l_g n \times W + m_r = 0$$

according to which:

$$m_r = -l n \times f_t - l_g n \times W,$$

$f_t$ represents a force acting on a tip of the surgical tool,
$f_p$ represents a force acting on a pivot position of the surgical tool,
$f_r$ represents a force acting on a rear end of the surgical tool,
W represents a force acting on a center of gravity of the surgical tool,
$m_r$ represents a moment produced in the joint portion,
$ln \times f_t$ represents a moment resulting from $f_t$,
$l_p n \times f_p$ is a moment resulting from $f_p$, and
$l_n n \times W$ is a moment resulting from W.

9. The method according to claim 8, wherein the surgical tool comprises a leading end portion configured to pinch a target tissue, and the bend portion is arranged between the leading end portion and the joint portion.

10. The method according to claim 8, wherein the surgical tool actuator comprises a gas-pressure actuator configured to generate the bend portion driving force with an externally supplied gas.

11. A computer program product comprising a non-transitory computer readable medium having stored thereon a program executable by a computer processor for controlling an arm device with a rotating joint portion, wherein the arm device supports a surgical tool and is configured to control a position and/or a posture of the surgical tool, the surgical tool comprises a bend portion, the bend portion being configured to bend in a transverse direction away from a longitudinal direction of the surgical tool, and the surgical tool comprises a surgical tool actuator configured to generate a bend portion driving force that bends the bend portion;
wherein the program, when executed by the computer processor, causes the computer processor to perform the following functions:

estimating an external force applied to the surgical tool;
obtaining a value of an actuator driving force that exerts a torque generated by a rotary actuator based on a weight of the surgical tool and the estimated external force applied to the surgical tool;
controlling the actuator driving force based on the obtained value of the actuator driving force, wherein the actuator driving force is configured to rotate the joint portion; and
estimating the external force applied to the surgical tool using information on a load supplied to the surgical tool actuator; and
wherein forces acting on the arm device satisfy the following formulas:

$$f_t + f_p + f_r + W = 0$$

$$ln \times f_t + l_p n \times f_p + l_g n \times W + m_r = 0$$

according to which:

$$m_r = -ln \times f_t - l_g n \times W$$

$f_t$ represents a force acting on a tip of the surgical tool,
$f_p$ represents a force acting on a pivot position of the surgical tool,
$f_r$ represents a force acting on a rear end of the surgical tool,
W represents a force acting on a center of gravity of the surgical tool,
$m_r$ represents a moment produced in the joint portion,
$ln \times f_t$ represents a moment resulting from $f_t$,
$l_p n \times f_p$ is a moment resulting from $f_p$, and
$l_g n \times W$ is a moment resulting from W.

12. The computer program product of claim 11, wherein the surgical tool comprises a leading end portion configured to pinch a target tissue, and the bend portion is arranged between the leading end portion and the joint portion.

13. The computer program product of claim 11, wherein the surgical tool actuator comprises a gas-pressure actuator configured to generate the bend portion driving force with an externally supplied gas.

* * * * *